US011287378B2

(12) United States Patent
Favero et al.

(10) Patent No.: US 11,287,378 B2
(45) Date of Patent: Mar. 29, 2022

(54) METHOD FOR ASSAYING CATIONIC POLYMERS BY TIME-RESOLVED PHOTOLUMINESCENCE

(71) Applicant: SPCM SA, Andrezieux-Boutheon (FR)

(72) Inventors: Cédrick Favero, Andrezieux-Boutheon (FR); Renaud Souzy, Andrezieux-Boutheon (FR); Olivier Braun, Andrezieux-Boutheon (FR); Alexis Guillard, Andrezieux-Boutheon (FR)

(73) Assignee: SPCM SA, Andrezieuix-Bouthbon (FR)

( * ) Notice: Subject to any disclaimer, the term of this patent is extended or adjusted under 35 U.S.C. 154(b) by 306 days.

(21) Appl. No.: 16/495,968

(22) PCT Filed: Feb. 21, 2018

(86) PCT No.: PCT/FR2018/050412
§ 371 (c)(1),
(2) Date: Sep. 20, 2019

(87) PCT Pub. No.: WO2018/178528
PCT Pub. Date: Oct. 4, 2018

(65) Prior Publication Data
US 2020/0132602 A1    Apr. 30, 2020

(30) Foreign Application Priority Data

Mar. 27, 2017  (FR) ...................................... 1752540

(51) Int. Cl.
*G01N 21/64*      (2006.01)
*G01N 33/58*      (2006.01)
(Continued)

(52) U.S. Cl.
CPC ....... *G01N 21/6408* (2013.01); *G01N 21/643* (2013.01); *G01N 33/18* (2013.01); *G01N 33/2835* (2013.01); *G01N 33/582* (2013.01)

(58) Field of Classification Search
CPC ............... G01N 21/6408; G01N 33/18; G01N 33/2835; G01N 21/643; G01N 33/582; G01N 33/542
See application file for complete search history.

(56) References Cited

U.S. PATENT DOCUMENTS

| 6,077,461 A * | 6/2000 | Murray ................. C08F 220/36 252/700 |
| 2011/0183435 A1* | 7/2011 | Yang ..................... C08F 290/00 436/501 |
| 2012/0270328 A1* | 10/2012 | Zhang .................... G01N 21/49 436/85 |

(Continued)

FOREIGN PATENT DOCUMENTS

| FR | 2868783 A1 | 10/2005 |
| WO | 2009127893 A1 | 10/2009 |

(Continued)

OTHER PUBLICATIONS

Translation of WO2016203119A1, Hurtevent, Christian, Dec. 22, 2016 (Year: 2016).*

(Continued)

*Primary Examiner* — Samuel P Siefke
*Assistant Examiner* — Henry H Nguyen
(74) *Attorney, Agent, or Firm* — Dilworth IP, LLC

(57) ABSTRACT

The present invention concerns a method for determining the concentration of cationic polymers present in a sample, according to the following steps: —bringing the cationic polymer or polymers present in the sample into contact with, and enabling the interaction thereof with, a developer solution comprising lanthanide (III) ions and at least one bonding agent, and —exciting the sample at an excitation wavelength $\lambda_{exc}$ and detecting, by time resolved photoluminescence, a signal originating from the lanthanide (III) ions having interacted with the at least one bonding agent having previously interacted with the cationic polymer or polymers, at an emission wavelength $\lambda_{em}$, and —determining the cationic polymer concentration of the sample by using the signal detected at the emission wavelength $\lambda_{em}$, the sample originating from water originating from municipal or industrial water or sludge treatment processes.

9 Claims, 2 Drawing Sheets

(51) Int. Cl.
*G01N 33/28* (2006.01)
*G01N 33/18* (2006.01)

(56) References Cited

U.S. PATENT DOCUMENTS

2016/0122201 A1* 5/2016 Gilmore ............. G01N 33/1806
                                                    700/271
2016/0274079 A1* 9/2016 Harma ................. G01N 33/542
2016/0290923 A1* 10/2016 Nuutinen ............... G01N 21/77

FOREIGN PATENT DOCUMENTS

| WO | 2015075308 | A1 | 5/2015 |
| WO | 2015092311 | A1 | 6/2015 |
| WO | 2016203119 | A1 | 12/2016 |

OTHER PUBLICATIONS

James Johnstone et al.; "Novel Method for Real-Time Monitoring of Scale Control Products at the Site of Use"; May 14, 2014; SPE International; pp. 1-10.
Thomas Brichart et al.; "The Use of Fluorescent Tracers for Inhibitor Concentration Monitoring Useful for Scale Inhibitor Squeeze Evaluation"; International Petroleum Technology Conference; Dec. 10, 2014; pp. 1-8.
Eva F Gudgin Dickson et al.; "Ultrasensitive bioanalytical assays using time-resolved fluorescence detection"; Jan. 1, 1995; Pharmac. Ther. vol. 66, pp. 207-235.
PCT International Search Report dated Apr. 18, 2018 in corresponding Application No. PCT/FR2018/050412, 3 pages.

* cited by examiner

METHOD FOR ASSAYING CATIONIC POLYMERS BY TIME-RESOLVED PHOTOLUMINESCENCE

FIELD OF THE INVENTION

The present invention concerns a method for assaying cationic polymers. More specifically, the present invention concerns a method for assaying cationic polymers in a sample using time-resolved photoluminescence. This sample originates from water obtained from water treatment processes or from municipal or industrial sludge.

BACKGROUND OF THE INVENTION

Cationic polymers are used in various fields such as the treatment of industrial and drinking water, the paper industry, during the various stages of mining extraction (drilling, mining discharges, purification and recycling), sludge treatment, or the enhanced recovery of oil and gas. In these different fields, it is important for the person skilled in the art to know the concentration of cationic macromolecular additives (flocculants, coagulants, friction reducers, rheological additives, etc.) to avoid any undesirable occurrences such as the discharge of water containing cationic residues into nature, unwanted interference with other additives, or simply for the adjustment of the cationic polymer concentrations in formulations of petroleum-based fluids, for application in paper production and water treatment.

In addition, it is essential for the person skilled in the art to know the cationic polymer concentration, since under- or overdosing can lead to changes in their application performance in formulations such as viscosification, flocculation, compatibility, friction reduction as well as environmental problems and additional production costs.

Nowadays, a variety of analytical techniques are currently used to determine the concentration of cationic polymers. Examples of techniques include colloidal titration, NMR spectroscopy, a flocculation test, or iodine titration.

However, these methods are very restrictive because, for the most part, a relatively pure sample is essential, which requires complex purification steps. Moreover, it is not possible to determine very low concentrations of polymers using these methods. Indeed, polymer concentrations below 10 ppm cannot be determined using most of these methods.

There is therefore a need for a method for assaying cationic polymers in a sample.

DISCLOSURE OF THE INVENTION

The present invention concerns a method for determining the concentration of cationic polymer(s) present in a sample. This method comprises the following steps:
- optionally, pre-treating the sample,
- bringing the cationic polymer(s) present in the sample into contact with, and enabling the interaction thereof with, a developer solution comprising lanthanide (III) ions and at least one bonding agent,
- exciting the sample at an excitation wavelength of $\lambda_{exc}$ and detecting, by time-resolved photoluminescence, a signal originating from the lanthanide (III) ions having interacted with at least one bonding agent having previously interacted with the cationic polymers at an emission wavelength $\lambda_{em}$, and
- determining the concentration of the cationic polymer(s) of the sample by using the signal detected at the emission wavelength $\lambda_{em}$.

The sample used originates from water obtained from water treatment processes or from municipal or industrial sludge.

The term "cationic polymer", refers to a polymer or copolymer having a positive overall charge that necessarily contains at least one cationic monomer. In other words, when the polymer contains anionic and/or non-ionic monomers, the amount of cationic charges is greater than the amount of anionic charges.

The term "lanthanide (III) ions" refers to lanthanide (III) ions of the same lanthanide or several different lanthanides.

The method according to the present invention can be used to determine the concentration of cationic polymer(s) present in samples from water treatment processes or mineral or organic sludge.

However, the method of the present invention can also be used to determine the concentration of cationic polymer(s) present in samples from underground formations such as oil or gas wells; treatment processes for water or sludge, mineral or organic; cosmetics; detergents; paper manufacturing; or the mining industry.

Surprisingly, it was discovered that by using the method of the invention, the signal obtained by time-resolved photoluminescence from the product of the interaction between the cationic polymer(s) and the developer solution comprising the lanthanide ions precisely correlates with the concentration of the cationic polymer(s) present in a sample.

According to the invention, the time-resolved photoluminescence measurement that is preferably used is the time-resolved fluorescence measurement.

This method is ideal for polymers with a molecular weight advantageously between 1,000 and 15 million g/mol. Unless otherwise specified, the "molecular weight" of a polymer refers to the weight average molecular weight.

According to the invention, the polymer may be a natural polymer or a synthetic polymer. It may be a natural polymer that can be selected from polysaccharide derivatives such as starch, guar, cellulose, dextran or xanthan.

According to the invention, the polymer may also be a polycondensate of a cationic polyamine. Cationic polyamines can be obtained according to the document WO 2009/127893. The manufacturing process mainly uses two families of additives:
- water-soluble secondary amines of dimethylamines, diethylamines or dipropylamines, a mixture of secondary amines the alkyl groups thereof contain between 1 and 3 carbon atoms,
- difunctional epoxides polycondensable in the presence of amines, such as epibromohydrin, epichloroidrin, or epiiodohydrin.

Advantageously, these polycondensates are quaternary ammonium polyamines and may be derived from the polycondensation of epichlorohydrin and dimethylamine, dicyandiamide or melamine and formaldehyde.

According to the invention, the cationic polymer can be obtained using well-known processes of conventional free-radical polymerization in bulk, in a solution, an emulsion, a suspension, or by controlled free-radical polymerization techniques.

Advantageously, the sample comprises at least one cationic polymer having one or more cationic charge(s). Advantageously, all the polymers present in the sample comprise one or more cationic charges(s). The sample is advantageously of an aqueous composition containing at least one cationic polymer.

The cationic polymer may be a copolymer formed from at least two or more monomers. According to the invention, the polymer may have a linear, branched, cross-linked, star-shaped or comb-shaped structure.

According to the invention, the sample contains at least one cationic polymer that may have originated from the (co)polymerization of at least one cationic monomer and optionally at least one non-ionic monomer (A) and/or at least one anionic or zwitterionic monomer. The cationic monomer is advantageously water soluble.

The cationic monomer may be of the acrylamide, acrylic, vinylic, allylic or maleic type having a quaternary amine or ammonium function. Mention may be made, in particular and in a non-limiting way, of quaternized or salified dimethylaminoethyl acrylate (DMAEA), and dimethylaminoethyl methacrylate (DMAEMA), dimethyldiallylammonium chloride (DADMAC), acrylamido propyltrimethyl ammonium chloride (APTAC) and methacrylamido propyltrimethyl ammonium chloride (MAPTAC). The cationic monomers derived from acrylamide and carrying a hydrophobic chain described in document FR U.S. Pat. No. 2,868,783 may be used.

According to a particular embodiment, the polymer advantageously comprises between 1 and 100 mol % of cationic monomer(s), preferably between 10 and 100 mol %, relative to the total number of moles of monomers of the cationic polymer.

The monomer (A) may be a non-ionic monomer that notably can be selected from the group comprising water-soluble vinyl monomers, and particularly acrylamide; methacrylamide; N-isopropylacrylamide; N,N-dimethylacrylamide; N-vinylformamide; acryloyl morpholine; N,N-diethyl acrylamide; N-tert-butyl acrylamide; N-tert-octylacrylamide; N-vinylpyrrolidone; N-vinylcaprolactam; N-vinyl-imidazole; and diacetone acrylamide.

The non-ionic monomer can also be chosen from monomers with formula:

D-Z-D' where:
D is an unsaturated polymerizable chemical functional group of type acrylate, methacrylate, acrylamide, methacrylamide, vinyl or allylic,
D' represents hydrogen or an alkyl group (preferably $C_1$-$C_{22}$) or an aryl group (preferably $C_1$-$C_{22}$),
Z has the following structure: —(OE)w-(OP)x-(OBu)z-
where:
  OE, OP, OBu denote ethylene oxide, propylene oxide and butylene oxide respectively,
  the arrangement between the various OE and/or OP and/or OBu units can be statistical, alternating, gradient, or block,
  w, x and z are integers between 0 and 150 and w+x+z≠0.

According to a particular embodiment, the polymer advantageously comprises between 0 and 99 mol % of non-ionic monomer(s), preferably between 0 and 90 mol % relative to the total number of moles of monomers.

The anionic monomer(s) can be chosen from a large group. Advantageously it is a water-soluble monomer, i.e., a monomer soluble in water under conventional polymerization conditions. These monomers may have acrylic, vinyl, maleic, fumaric, malonic, itaconic, or allylic functions. They may contain a carboxylate, phosphonate, phosphate, sulfate, sulfate, sulfonate, or another anionically charged group. The anionic monomer may be in the form of an acid or in the form of an alkaline earth metal or alkali metal salt. Examples of suitable monomers include acrylic acid; methacrylic acid; itaconic acid; crotonic acid; maleic acid; fumaric acid; monomers of the strong acid type having for example a function of the sulfonic acid or phosphonic acid type, such as 2-acrylamido-2-methylpropane sulfonic acid, vinylsulfonic acid, vinylphosphonic acid, allylsulfonic acid, allylphosphonic acid, or styrenesulfonic acid; and the water-soluble alkali metal, alkaline earth metal, or ammonium salts thereof.

According to a particular embodiment, the polymer advantageously comprises between 0 and 49 mol % of anionic monomer(s), preferably between 0 and 30 mol %, relative to the total number of moles of monomers.

According to the invention, the cationic polymer is very specifically a coagulant and/or a flocculant and/or a thickener and/or a friction-reducing additive. It should be noted that the polymers concerned in said invention are totally different from deposit or corrosion inhibitors in terms of function, mechanism of action and macromolecular morphology. Indeed, the functions and mechanisms of action of the coagulants in the fluid are to suppress the inter-colloidal repulsions and to allow the agglomeration and sedimentation of the colloidal particles (mineral and/or organic). The flocculants enable the agglomeration of small particles and/or coagulated aggregates and thus the formation of filterable flocs. Thickeners increase the viscosity of aqueous fluids. The role of cationic friction reducers is to limit the friction forces between an aqueous fluid and the inner wall of a pipe (lowering the fluid turbulence). The functions of coagulants, flocculants, thickeners and friction reducers are therefore very different from deposit and/or corrosion inhibitors that rely instead on the reinforcement of the electrostatic and/or electro-steric interactions between metal/mineral particles.

According to the invention, the developer solution includes lanthanide (III) ions and at least one bonding agent.

The lanthanide (III) ions are advantageously chosen from europium, terbium, samarium or dysprosium ions. Preferably, the lanthanide (III) ions are europium ions or terbium ions. In the developer solution, the lanthanide (III) can be a lanthanide salt, for example a lanthanide halide such as europium chloride.

The bonding agent enabling the link between a lanthanide cation and a cationic polymer is advantageously an anionic agent comprising at least 2 anionic functions. Preferably, the bonding agent comprises more than 2 complexing functions with at least 4 to 4,000 anionic functions. More preferably, the binding agent has a polyelectrolyte-type polymer structure with a weight-average molar mass between 500 and 100,000 g/mol and with at least 10 to 2,000 anionic functions per polyelectrolyte chain.

Advantageously, the polyelectrolyte comprises chemical groups having fluorescence properties and enabling amplification of the detection signal. For this, fluorescent monomers can be used in the manufacture of the polyelectrolyte. Thus, the polyelectrolyte can be functionalized with sulfate, sulfonic, phosphate, phosphonic, carboxylic, imidazole, functional aryl macrocycle, and heteroaryl macrocycle groups, in their neutralized or acidic forms, and mixtures thereof.

The bonding agents are advantageously selected from sulfonated or non-sulfonated poly(carboxylic acids), poly(acetic)amine derivatives, copolymers of sulfonated monomers, and nitrogenous macrocycles functionalized with carboxylic acid groups. Preferably, the bonding agent is a copolymer of styrene sulfonic acid and maleic acid. This polymer is described in the patent WO2015/092311 as FL1.

According to a particular embodiment, the developer solution may comprise one or more buffer solutions to improve the signal-to-noise ratio of the samples analyzed.

Examples of buffers that can be used include sulfonic acid derivatives, such as for example HEPES (2-[4-(2-hydroxyethyl) piperazin-1-yl]ethanesulfonic acid, pKa 7.48), PIPES (1,4-piperazinediethanesulfonic acid, pKa 6.76), MOPS (3-morpholinopropane-1-sulfonic acid, pKa 7.2) and MES (2-(N-morpholino)ethanesulfonic acid, pKa 6.15). Preferably, the buffer is HEPES. Developer solutions that can be used include those sold by the Glincs company.

The developer solution is advantageously an aqueous solution.

According to another particular embodiment of the invention, one or more buffers, mentioned above, can be added to the sample before signal detection at the emission wavelength $\lambda_{em}$, in order to improve the signal-to-noise ratio and the signal-to-background noise ratio of the signals from the detected samples.

The quantity of lanthanide (III) ions added to the sample is advantageously between 1 ppm and 10,000 ppm, preferably between 5 ppm and 1000 ppm. The amount of lanthanide (III) ions is expressed in weight relative to the weight of the sample before the sample comes into contact with the developer solution.

According to the invention, the concentration of cationic polymer(s) is quantified, using a time-resolved photoluminescence method that is described in particular in the article, "*Ultrasensitive Bioanalytical Assays Using Time-Resolved Fluorescence Detection*", Pharmacol. Ther., Vol. 66(2), pages 207-35, 1995. This is based on the application of a time delay, known as the integration time, between the excitation of the sample to be analyzed and the measurement of the signal emitted, in order to avoid short-lifetime parasitic photoluminescences. This method can be used at room temperature, notably with a device like the Cary Eclipse from Agilent.

The wavelength used in the invention can be selected or determined by studying the maximum excitation in the excitation spectrum of the product of the interaction between the cationic polymer(s) and the developer solution comprising lanthanide (III) ions. For example, the excitation wavelength $\lambda_{exc}$ can be between 200 nm and 600 nm and the emission signal wavelength $\lambda_{em}$ can be between 300 nm and 800 nm.

The integration time can be between 0.001 ms and 10 ms (ms=milliseconds), preferably between 0.01 and 5 ms, and more preferably between 0.1 and 3 ms. In some cases, the longer this time period, the better the signal-to-noise ratio, improving the reliability of the measurement. The photon collection time can range from 5 to 10 ms, for example.

The sample may optionally be pre-treated prior to determining the concentration of cationic polymer(s). This pre-treatment can be useful when the sample includes salts, for example inorganic salts present in production water, or insoluble particles. Production water is water recovered after water/hydrocarbon separation in an oil or gas recovery process. This pre-treatment may also be useful when the sample comes from water that originates from a manufacturing process of paper sheets and/or cardboard, a coagulation and/or flocculation process of industrial and/or drinking water, a treatment process, coagulation, flocculation of sludge from a treatment plant of industrial and/or drinking water.

According to one embodiment of the invention, the method comprises a sample purification step before the addition of the developer solution comprising the lanthanide (III) ions and the bonding agents. Thus, the sample can be purified to eliminate substances and/or compounds that may interfere with the signal measured at the emission wavelength $\lambda_{em}$. For example, pre-cleaning can help minimize the background noise caused by the components of the sample. Purification processes that can be used in the invention include centrifugation, size exclusion chromatography, cleaning with solid phase extraction cartridges (SPEs), dialysis techniques, extraction methods for the removal of hydrocarbons, filtration, microfiltration, ultrafiltration, nanofiltration, membrane centrifugation and/or other methods for separating polymeric species with small molecular weights (advantageously less than 1,000 g/mol).

In one embodiment of the invention, the salt concentration of the sample may be modified and/or the insoluble particles may be removed before adding the developer solution comprising the lanthanide (III) ions. Modifying the salt concentration of the sample may increase or decrease the salt concentration before the developer solution containing lanthanide (III) ions is added.

According to one particular embodiment of the invention, if the sample is too viscous because of an initial concentration of cationic polymer(s) that is too high, the sample may be diluted before the addition of the developer solution comprising lanthanide (III) ions. Diluents can be chosen from water, aqueous buffer solutions, saline solutions that may or may not be saturated in salts, or mixtures thereof.

According to a particular embodiment of the invention, one or more of the above pre-treatment steps can be performed on a sample before measuring the concentration of cationic polymer(s) in a sample. For example, prior to measurement, the sample can be purified and/or diluted.

In a particular embodiment of the invention, the pH value of the sample is adjusted to an appropriate level. The pH of the sample is advantageously between 3 and 10, preferably between 5 and 8. Any appropriate buffer that does not significantly interfere with the detection of the sample signal can be used. Examples of buffers are given above, but other buffers can also be used.

To determine the concentration of cationic polymers, a standard curve or standard points may be prepared before using the determination method according to the invention. The concentration of cationic polymers can be calculated from the signal by referring to the standard curve or predetermined standard points. Alternatively, the measuring instrument can be pre-calibrated.

The following protocol for the assaying of cationic polymers can be followed:

1) Solutions of known concentrations of cationic polymer are prepared by successive dilution of a stock solution of cationic polymer with water having advantageously the characteristics (in particular salinity and conductivity) of sample X of unknown concentration. The samples from each series are then diluted with a lanthanide developer solution and analyzed by Time-Resolved Fluorescence (TRF). The measurement parameters as well as the emission and excitation wavelengths are adjusted according to the type of lanthanide.

2) For each series, the TRF Signal Intensity vs Molar Concentration are extrapolated and an TRF vs Concentration calibration curve is developed.

3) Sample X is then diluted with the developer solution. The TRF intensity is measured.

4) After correlation of the TRF intensity of sample X with the cationic concentration calibration line in 2), the previously unknown cationic polymer concentration of sample X is deduced.

The dilution steps can be performed by adding water.

However, when the sample comes from production water, all dilution steps can be performed with a brine that has the same conductivity and salinity characteristics as the production water, even for standard polymers.

It is important to note that it is also possible to determine the cationic charge density of the polymer by extrapolating the slope of the TRF Signal Intensity vs. Dilution Rate curve and correlating with the slope of the Intensity vs. Dilution variation curve of polymer stock solutions of known cationicity. In general, any time-resolved photoluminescence technique can replace TRF, in particular for steps 1) to 4) above.

The invention and the advantages deriving therefrom will be better understood from the following figures and examples provided as a non-limiting illustration of the invention.

EXAMPLE EMBODIMENTS OF THE INVENTION

The following abbreviations are used:
DADMAC: Diallyl dimethyl ammonium chloride, $[(CH_3)_2N^+(CH_2CH=CH_2)_2]Cl^-$
AM: Acrylamide, $CH_2=CH-C(=O)-NH_2$
ADAME quat: Trimethylammonium ethyl chloride acrylate, $CH_2=CH-C(=O)-O-(CH_2CH_2)-N^+(CH_3)_3.Cl^-$
$\lambda_{em}$: Emission wavelength
$\lambda_{exc}$: Excitation wavelength

Example 1—Assaying of the Residual Concentration of a Coagulating Cationic Polymer in Industrial Effluent Water This example relates to the assaying of the residual concentration of a cationic coagulant of type poly(DADMAC), present in an industrial effluent water (conductivity of 385 µS.cm$^{-1}$ at 20° C.).

a) Preparation of Control Solutions

Solutions of known concentrations were prepared of poly(DADMAC) (trade name: Floquat FL4440-SNF) by successive dilution of a stock solution of polymer with water having the same chemical salt composition as the industrial water (Table 1).

TABLE 1

Concentration of control solutions of poly(DADMAC)

| Reference | Chemical composition | Concentration (ppm, by weight relative to the weight of the solution) |
|---|---|---|
| A0 | — | 0 |
| A1 | poly(DADMAC) | 0.4 |
| A2 | poly(DADMAC) | 0.8 |
| A3 | poly(DADMAC) | 1 |
| A4 | poly(DADMAC) | 1.5 |
| A5 | poly(DADMAC) | 2 |
| A6 | poly(DADMAC) | 4 |
| A7 | poly(DADMAC) | 6 |
| A8 | poly(DADMAC) | 8 |
| A9 | poly(DADMAC) | 10 |
| A10 | poly(DADMAC) | 15 |
| A11 | poly(DADMAC) | 20 |

The characteristics of the dilution water are:
Iron concentration: 103 µg/l
Chlorite concentration: 0.13 mg.l$^{-1}$
Sodium concentration: 145 mg.l$^{-1}$
Aluminum concentration: 133 µg.l$^{-1}$
Turbidity: 0.3 NFU b) Complexation with Developer Solutions Each of the solutions listed in Table 1 are diluted to 9/10 in a developer solution of europium associated with a copolymer of styrene sulfonic acid and maleic acid marketed by the company Glincs.

c) Time-Resolved Luminescence Measurement

Measurements are made at 20° C. in a quartz cuvette on a spectrometer like the Cary Eclipse Fluorescence Spectrophotometer from Agilent with the following characteristics:
75 kW Xenon flash lamp
Czerny-Turner monochromators
PM detector at 800 V
$\Delta_{pulse}=2$ µs The excitation spectra of the samples are performed between 200 and 450 nm. The emission wavelength is $\lambda_{em}=545$ nm.

The measurement parameters are set as follows:
Time: 0.1 ms
Photon collection time: 5 ms
Lamp frequency: 100 Hz
Number of flashes: 1

The analysis is started using the software controlling the spectrofluorometer.

d) Calibration Curve

The excitation spectra of the various solutions in Table 1 are performed at $\lambda_{exc}=260$ nm and $\lambda_{em}=610$ nm.

Figure 1:
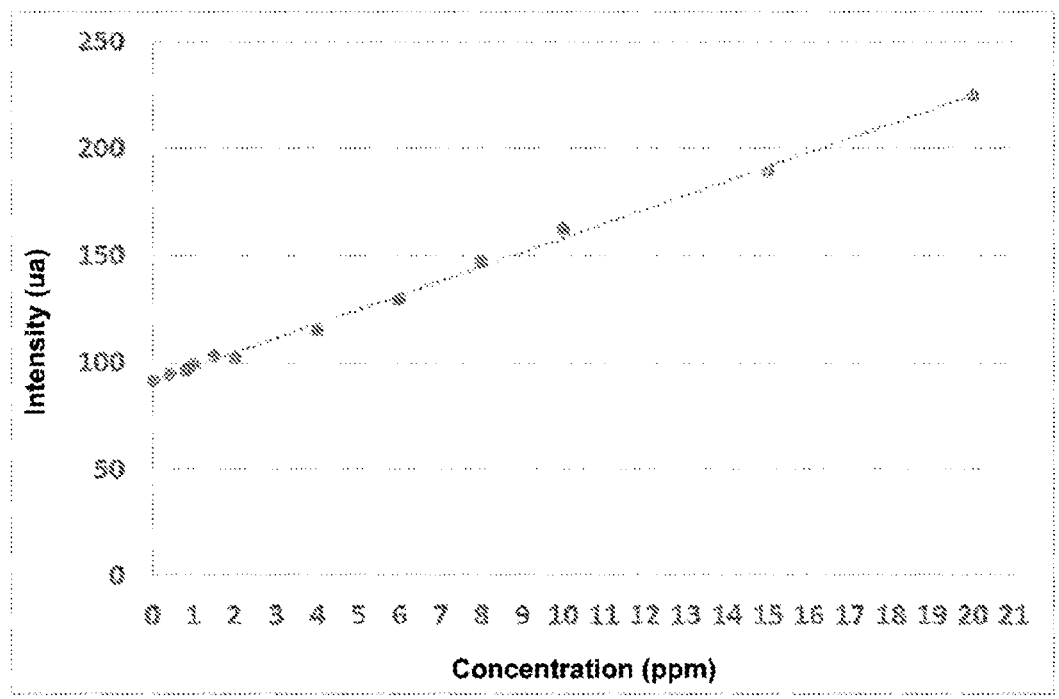
FIG. 1 shows the graph of the signal intensity at the emission wavelength $\lambda_{em}$ as a function of the poly(DADMAC) concentration.

The peak intensities as a function of concentration are shown in FIG. 1.

e) Assaying of the Coagulant Concentration of a Sample Taken from Industrial Effluent Water A sample of unknown concentration was taken from a volume of discharged industrial water.

This solution is diluted to 9/10 in a developer solution of europium associated with a copolymer of styrene sulfonic acid and maleic acid marketed by the company Glincs.

The measured intensity is 93.6 u.a. After extrapolation with the calibration line of Figure. 1, the coagulant concentration is deduced as 0.35 ppm by weight, relative to the weight of the sample.

This example demonstrates that it is possible to assay the cationic polymer concentration using time-resolved fluorescence techniques.

Example 2—Residual Assay of a Cationic Polyamine in Industrial Aggregate Wash Water This example relates to the assaying of the residual concentration of a cationic coagulant of type poly(quaternary amine) present in industrial water from aggregate washing.

a) Preparation of Control Solutions

The following solutions of different concentrations are prepared by successive dilution of a stock solution of poly(cationic amine) (trade name: Floquat FL2250-SNF) with water having the same salt and conductivity characteristics as the produced water.

TABLE 2

Composition of the control solutions of poly(cationic amine)

| Reference | Chemical composition | Concentration (ppm, by weight relative to the weight of the solution) |
|---|---|---|
| B0 | — | 0 |
| B1 | poly(cationic amine) | 0.5 |
| B2 | poly(cationic amine) | 1 |
| B3 | poly(cationic amine) | 1.5 |
| B4 | poly(cationic amine) | 2 |
| B5 | poly(cationic amine) | 5 |
| B6 | poly(cationic amine) | 10 |

The characteristics of the dilution water are:
Conductivity: 504 µS.cm$^{-1}$
Iron concentration: 185 µg/l b) Complexation with Developer Solutions Each of the solutions listed in Table 2 are diluted to 9/10 in a developer solution of europium associated with a copolymer of styrene sulfonic acid and maleic acid marketed by the company Glincs.

c) Time-Resolved Luminescence Measurement

Measurements are made at 20° C. in a quartz cuvette on a spectrometer like the Cary Eclipse Fluorescence Spectrophotometer from Agilent with the following characteristics:
75 kW Xenon flash lamp
Czerny-Turner monochromators
PM detector at 800 V
$\Delta_{pulse}$=2 µs The excitation spectra of the various solutions in Table 2 are performed at $\lambda_{exc}$=260 nm and $\lambda_{em}$=610 nm.

The measurement parameters are set as follows:
Time: 0.1 ms
Photon collection time: 5 ms
Lamp frequency: 100 Hz
Number of flashes: 1

The analysis is started using the software controlling the spectrofluorometer.

d) Calibration Curve

The excitation spectra of the various solutions in Table 2 are performed at $\lambda_{exc}$ 15=260 nm and $\lambda_{em}$=610 nm.

Figure 2:
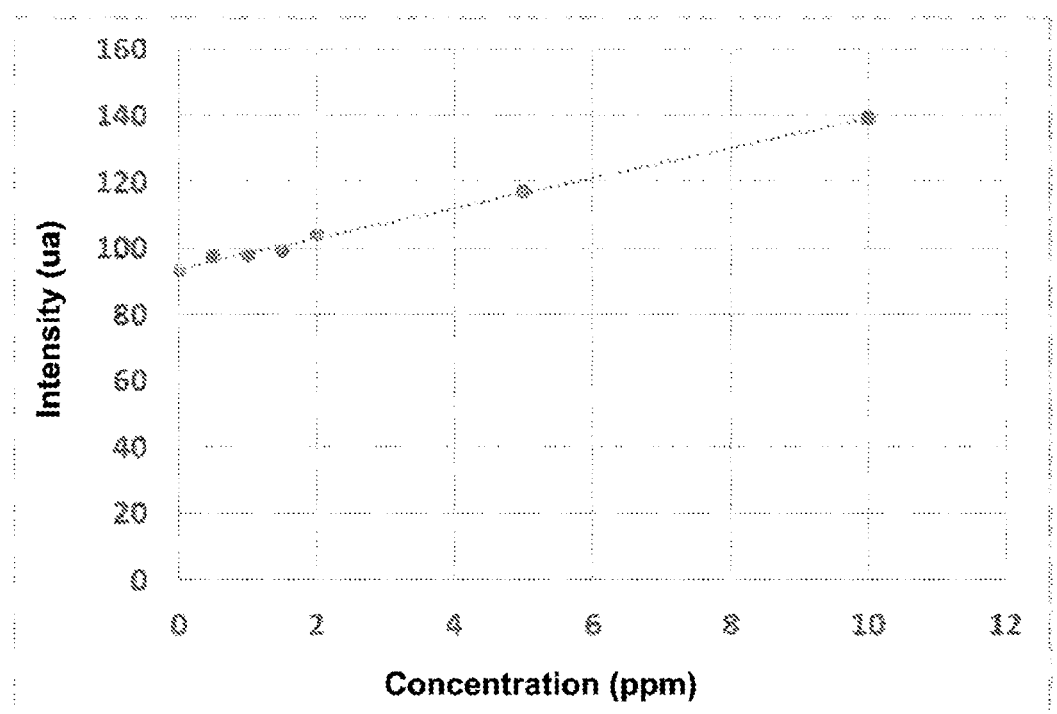
FIG. 2 shows the graph of the signal intensity at the emission wavelength $\lambda_{em}$ as a function of the concentration of cationic polyamine.

The linear variation of peak intensity as a function of concentration is presented in FIG. 2.

e) Assaying of the Concentration of a Poly(Cationic Amine) Sample

A sample of unknown concentration was taken from a volume of industrial aggregate wash water. The suspended macro-particles are filtered beforehand.

This solution is diluted to 9/10 in a developer solution of europium associated with a copolymer of styrene sulfonic acid and maleic acid marketed by the company Glincs.

The measured intensity is 94.2 u.a. After extrapolation with the calibration line of FIG. 1, the concentration of coagulant is deduced as 0.21 ppm.

This example demonstrates that it is possible to assay the concentration of cationic polymers having a chemical nature different to poly(DADMAC) using time-resolved fluorescence techniques.

Example 3—Residual Assay of a Flocculating Copolymer in Water Resulting from Industrial Sludge Flocculation This example relates to the assaying of the residual concentration of a cationic flocculant of type poly(AM-co-ADAME quat) with a very high weight-average molar mass present in industrial water resulting from the flocculation of industrial sludge from a purification plant.

a) Preparation of Control Solutions

The following solutions of different concentrations are prepared by successive dilution of a stock solution of poly(AM-co-ADAME quat) (trade name: Flopaam FO 4650 SSH-SNF) with water having the same salt and conductivity characteristics as the produced water.

TABLE 3

Composition of the control solutions of poly(AM-co-ADAME quat)

| Reference | Chemical composition | Concentration (ppm, by weight relative to the weight of the solution) |
|---|---|---|
| C0 | — | 0 |
| C1 | poly(AM-co-ADAME quat) | 0.5 |
| C2 | poly(AM-co-ADAME quat) | 1 |
| C3 | poly(AM-co-ADAME quat) | 2 |
| C4 | poly(AM-co-ADAME quat) | 3 |
| C5 | poly(AM-co-ADAME quat) | 5 |
| C6 | poly(AM-co-ADAME quat) | 7 |
| C7 | poly(AM-co-ADAME quat) | 10 |
| C8 | poly(AM-co-ADAME quat) | 12 |
| C9 | poly(AM-co-ADAME quat) | 14 |
| C10 | poly(AM-co-ADAME quat) | 18 |
| C11 | poly(AM-co-ADAME quat) | 20 |
| C11 | poly(AM-co-ADAME quat) | 40 |
| C12 | poly(AM-co-ADAME quat) | 60 |
| C13 | poly(AM-co-ADAME quat) | 80 |
| C14 | poly(AM-co-ADAME quat) | 100 |
| C14 | poly(AM-co-ADAME quat) | 200 |

The characteristics of the dilution water are:
Conductivity: 750 µS.cm$^{-1}$
Iron concentration: 215 µg/l b) Complexation with Developer Solutions Each of the solutions listed in Table 3 are diluted to 9/10 in a developer solution of europium associated with a copolymer of styrene sulfonic acid and maleic acid.

c) Time-Resolved Luminescence Measurement

Measurements are made at 20° C. in a quartz cuvette on a spectrometer like the Cary Eclipse Fluorescence Spectrophotometer from Agilent with the following characteristics:
75 kW Xenon flash lamp
Czerny-Turner monochromators
PM detector at 800 V
$\Delta_{pulse}$=2 µs The excitation spectra of the different solutions of Table 3 are performed at $\lambda_{exc}$=260 nm and $\lambda_{em}$=610 nm.

The measurement parameters are set as follows:
Time: 0.1 ms
Photon collection time: 5 ms
Lamp frequency: 100 Hz
Number of flashes: 1

The analysis is started using the software controlling the spectrofluorometer.

d) Calibration Curve

The excitation spectra of the different solutions of Table 3 are performed at $\lambda_{exc}$=260 nm and $\lambda_{em}$=610 nm.

Figure 3:
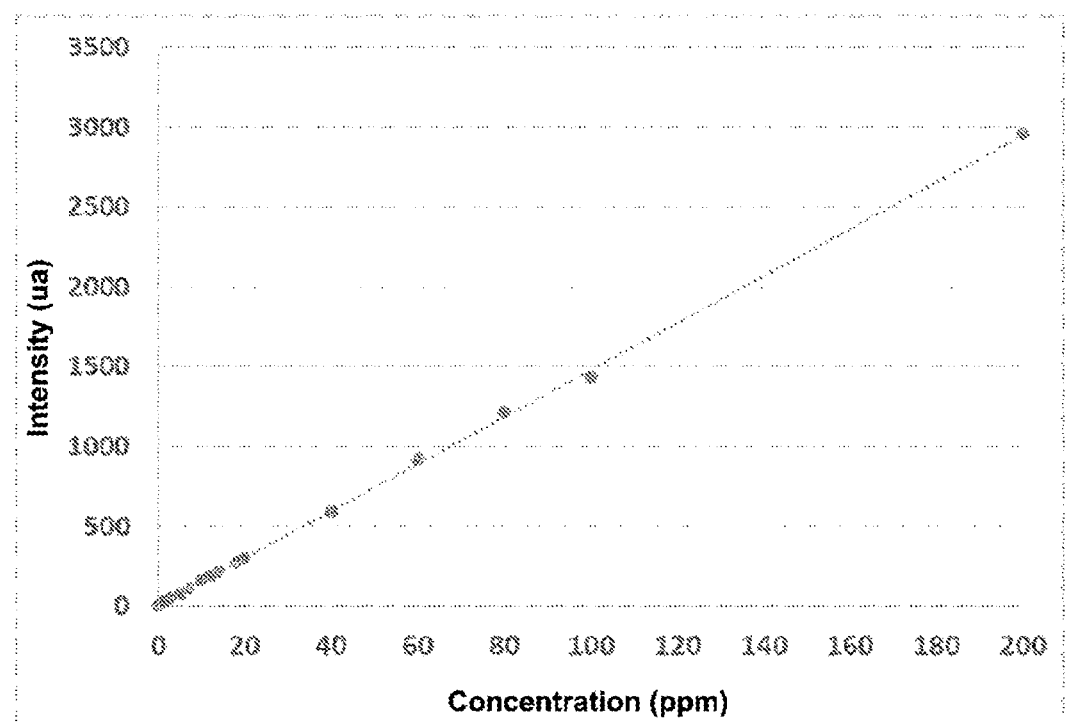
FIG. 3 shows the graph of the signal intensity at the emission wavelength ken, as a function of the concentration of poly(AM-co-ADAME quat).

The linear variation of peak intensity as a function of concentration is presented in FIG. 3.

e) Assaying of the Concentration of a Poly(AM-Co-ADAME Quat) Sample

A sample of unknown concentration was taken from a volume of industrial water resulting from the flocculation of industrial sludge from the purification plant. The suspended macro-particles are filtered beforehand.

This solution is diluted to 9/10 in a developer solution of europium associated with a copolymer of styrene sulfonic acid and maleic acid marketed by the company Glincs.

The measured intensity is 83.31 u.a. After extrapolation with the calibration line of FIG. 3, the flocculant concentration is deduced as 5.33 ppm.

This example demonstrates that it is possible to determine the concentration of flocculant cationic polymers of very high weight-average molar masses using time-resolved fluorescence techniques.

The invention claimed is:

1. A method for determining the concentration of cationic polymers present in a sample, according to the following steps:
    bringing the cationic polymers present in the sample into contact with, and enabling the interaction thereof with, a developer solution comprising lanthanide (III) ions and at least one bonding agent,
    exciting the sample at an excitation wavelength $\lambda_{exc}$ and detecting, by time-resolved photoluminescence, a signal from the lanthanide (III) ions that have interacted with the at least one bonding agent having previously interacted with the cationic polymers at an emission wavelength $\lambda_{em}$, and
    determining the cationic polymer concentration of the sample using the signal detected at the emission wavelength $\lambda_{em}$,
    the sample originating from water obtained from water treatment processes or from municipal or industrial sludge,
    wherein the at least one bonding agent is a copolymer of styrene sulfonic acid and maleic acid.

2. The method according to claim 1, wherein the time-resolved photoluminescence is time-resolved fluorescence.

3. The method according to claim 1, wherein the sample contains at least one polymer resulting from the polymerization of at least one cationic monomer and, optionally, at least one non-ionic monomer (A) and/or at least one anionic or zwitterionic monomer.

4. The method according to claim 1, wherein the lanthanide (III) ions are chosen from europium, terbium, samarium or dysprosium ions.

5. The method according to claim 4, wherein the lanthanide (III) ions are europium or terbium ions.

6. The method according to claim 1, wherein an amount of the lanthanide (III) ions between 1 ppm and 10,000 ppm is added to the sample by weight based on the weight of the sample before the sample comes into contact with the developer solution.

7. The method according to claim 1, wherein the excitation wavelength $\lambda_{exc}$ is between 200 nm and 600 nm, and the emission signal wavelength $\lambda_{em}$ is between 300 nm and 800 nm.

8. The method according to claim 1, wherein the at least one bonding agent is an anionic agent comprising at least 2 anionic functions.

9. The method according to claim 1, further comprising a sample purification step prior to adding the developer solution comprising the lanthanide (III) ions.

* * * * *